United States Patent
Gurumoorthy (10) Patent No.: US 12,042,606 B2
(45) Date of Patent: Jul. 23, 2024

(54) SYSTEMS, METHODS, AND DEVICES FOR BIOMARKER SHAPING AND SLEEP PROFILE ENHANCEMENT

(71) Applicant: StimScience Inc., Berkeley, CA (US)

(72) Inventor: Ram Gurumoorthy, Lafayette, CA (US)

(73) Assignee: STIMSCIENCE INC., Berkeley, CA (US)

(*) Notice: Subject to any disclaimer, the term of this patent is extended or adjusted under 35 U.S.C. 154(b) by 305 days.

(21) Appl. No.: 17/000,093

(22) Filed: Aug. 21, 2020

(65) Prior Publication Data

US 2022/0054794 A1  Feb. 24, 2022

(51) Int. Cl.
| | | |
|---|---|---|
| A61M 21/02 | (2006.01) | |
| A61N 1/04 | (2006.01) | |
| A61N 1/36 | (2006.01) | |
| A61M 21/00 | (2006.01) | |

(52) U.S. Cl.
CPC ........... *A61M 21/02* (2013.01); *A61N 1/0404* (2013.01); *A61N 1/36031* (2017.08); *A61N 1/36034* (2017.08); *A61M 2021/0027* (2013.01); *A61M 2021/0072* (2013.01)

(58) Field of Classification Search
CPC ..... A61M 21/02; A61B 5/4812; A61B 5/4815
See application file for complete search history.

(56) References Cited

U.S. PATENT DOCUMENTS

| | | | | |
|---|---|---|---|---|
| 2006/0106275 A1* | 5/2006 | Raniere | .................. | A61M 21/02 600/26 |
| 2013/0303837 A1* | 11/2013 | Berka | .................... | A61B 5/389 600/27 |
| 2016/0302718 A1* | 10/2016 | Laura Lapoint | ....... | A61B 5/375 |
| 2017/0000970 A1* | 1/2017 | Garcia Molina | ..... | A61M 21/02 |
| 2018/0092600 A1* | 4/2018 | Simons | .............. | A61N 1/36031 |
| 2018/0361110 A1 | 12/2018 | Garcia Molina et al. | | |
| 2019/0070386 A1* | 3/2019 | Raut | .................... | A61B 5/4812 |
| 2019/0231256 A1* | 8/2019 | Jantunen | .............. | A61B 5/4815 |
| 2019/0282812 A1* | 9/2019 | Simons | .................... | A61N 1/20 |

FOREIGN PATENT DOCUMENTS

EP  3957248  2/2022

OTHER PUBLICATIONS

"European Application Serial No. 21192252.1, Extended European Search Report dated Jan. 4, 2022", 16 pgs.
European Application Serial No. 21192252.1, Communication Pursuant to Article 94(3) EPC dated Oct. 30, 2023, 7 pgs.

* cited by examiner

*Primary Examiner* — Kaylee R Wilson
(74) *Attorney, Agent, or Firm* — SCHWEGMAN LUNDBERG & WOESSNER, P.A.

(57) ABSTRACT

Provided are systems, methods, and devices for biomarker shaping and sleep profile enhancement. Systems include a plurality of electrodes configured to be coupled to a brain of a user and configured to obtain a plurality of measurements from the brain of the user, and an interface configured to obtain the plurality of measurements from at least the plurality of electrodes. Systems also include a processing device comprising one or more processors configured to generate a first target sleep profile for the user based, at least in part, on the plurality of measurements and a plurality of biomarkers, the processing device being further configured to generate a plurality of stimulus parameters based, at least in part, on the target profile.

20 Claims, 6 Drawing Sheets

SYSTEMS, METHODS, AND DEVICES FOR BIOMARKER SHAPING AND SLEEP PROFILE ENHANCEMENT

TECHNICAL FIELD

The present disclosure relates to mechanisms and processes directed to measurements of brain activity and the enhancement of sleep.

BACKGROUND

A human brain may include neurons which exhibit measurable electrical signals when active. Accordingly, various measuring modalities, such as electrodes, may be used to measure such electrical activity. The neural activity of neurons may include many a variety of frequency components. Accordingly, such electrical activity may be measured and represented as a power spectrum in a frequency domain. Similarly, the other biometric measurements may be made as well. However, traditional techniques for measuring these activities remain limited in their ability to utilize such measurements, and more specifically, to efficiently and effectively utilize such measurement to enhance a user's sleep.

SUMMARY

Provided are systems, methods, and devices for biomarker shaping and sleep profile enhancement. Disclosed herein are systems including a plurality of electrodes configured to be coupled to a brain of a user and configured to obtain a plurality of measurements from the brain of the user, and an interface configured to obtain the plurality of measurements from at least the plurality of electrodes. Systems also include a processing device comprising one or more processors configured to generate a first target sleep profile for the user based, at least in part, on the plurality of measurements and a plurality of biomarkers, the processing device being further configured to generate a plurality of stimulus parameters based, at least in part, on the target profile.

In some embodiments, the target sleep profile is a sleep profile is an ideal sleep profile for the user. In various embodiments, the ideal sleep profile is identified based, at least in part, on a plurality of sleep stages and biomarkers identifying each of the plurality of sleep stages. According to some embodiments, the plurality of biomarkers comprises a ratio of band activities, shifts in frequency spectra of activity, and a dominant rational map of the user. In some embodiments, the plurality of stimulus parameters comprises frequencies and amplitudes of stimulation. In various embodiments, a controller comprising one or more processors configured to generate a control signal based on the plurality of stimulus parameters. According to some embodiments, the controller is further configured to use the control signal stimulate to the brain of the user via the plurality of electrodes and based on the plurality of stimulation parameters. In some embodiments, the processing device is further configured to generate a second target sleep profile after the stimulation of the brain of the user. In various embodiments, the plurality of electrodes is placed on a scalp of the user.

Also disclosed herein are devices including an interface configured to obtain a plurality of measurements from a plurality of electrodes configured to be coupled to a brain of a user, and a processing device comprising one or more processors configured to generate a first target sleep profile for a user based, at least in part, on the plurality of measurements and a plurality of biomarkers, the processing device being further configured to generate a plurality of stimulus parameters based, at least in part, on the target profile. Devices further include a controller comprising one or more processors configured to generate a control signal based on the plurality of stimulus parameters.

In some embodiments, the target sleep profile is a sleep profile is an ideal sleep profile for the user, and wherein the ideal sleep profile is identified based, at least in part, on a plurality of sleep stages and biomarkers identifying each of the plurality of sleep stages. In various embodiments, the plurality of biomarkers comprises a ratio of band activities, shifts in frequency spectra of activity, and a dominant rational map of the user. According to some embodiments, the plurality of stimulus parameters comprises frequencies and amplitudes of stimulation. In some embodiments, the controller is further configured to use the control signal stimulate to the brain of the user via the plurality of electrodes and based on the plurality of stimulation parameters.

Further disclosed herein are methods including receiving, via an interface and a plurality of electrodes coupled to a brain of a user, a plurality of measurements from the brain of the user, generating, using one or more processors of a processing device, a first target sleep profile for the user based, at least in part, on the plurality of measurements and a plurality of biomarkers, and generating, using one or more processors of the processing device, a plurality of stimulus parameters based, at least in part, on the target profile.

In some embodiments, the target sleep profile is a sleep profile is an ideal sleep profile for the user, and the ideal sleep profile is identified based, at least in part, on a plurality of sleep stages and biomarkers identifying each of the plurality of sleep stages. In various embodiments, the plurality of biomarkers includes a ratio of band activities, shifts in frequency spectra of activity, and a dominant rational map of the user. According to some embodiments, the plurality of stimulus parameters includes frequencies and amplitudes of stimulation. In some embodiments, methods further include generating, using a controller, a control signal based on the plurality of stimulus parameters. In various embodiments, methods additionally include stimulating, using the control signal, the brain of the user via the plurality of electrodes and based on the plurality of stimulation parameters. This and other embodiments are described further below with reference to the figures.

DETAILED DESCRIPTION OF EXAMPLE EMBODIMENTS

Reference will now be made in detail to some specific examples including the best modes contemplated by the inventors. Examples of these specific embodiments are illustrated in the accompanying drawings. While the present disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims. In addition, although many of the components and processes are described below in the singular for convenience, it will be appreciated by one of skill in the art that multiple components and repeated processes can also be used to practice the techniques of the present disclosure.

In the following description, numerous specific details are set forth in order to provide a thorough understanding of the present invention. Particular embodiments may be implemented without some or all of these specific details. In other instances, well known process operations have not been described in detail in order not to unnecessarily obscure the disclosure.

Human sleep can be measured using several aspects of the human physiology including their brain activity, heart activity, eye activity, temperature, movement, oxygen saturation, as well as various others. In various embodiments, measurements may include various observed metrics, as well as combinations of such observed metrics. For example, measurement data for heart rate activity may include the heart rate (mean, minimum or maximum over a period, mean square over a period, etc.) as well as the heart rate variability (beat-to-beat, or beat-to-beat aggregated over a window of time, etc.).

As will be discussed in greater detail below, various embodiments disclosed herein are configured to provide biomarker shaping and sleep enhancement. Thus, according to some embodiments, measurements are obtained and used to generate target sleep profiles for a user, as well as determine appropriate stimuli to be applied to the user to achieve such a target sleep profile. As will be discussed in greater detail below, sleep profiles may have associated biomarkers. Accordingly, stimulation may be applied to modify and shape the biomarkers to achieve a target sleep profile, and enhance a user's sleep.

Figure 1:
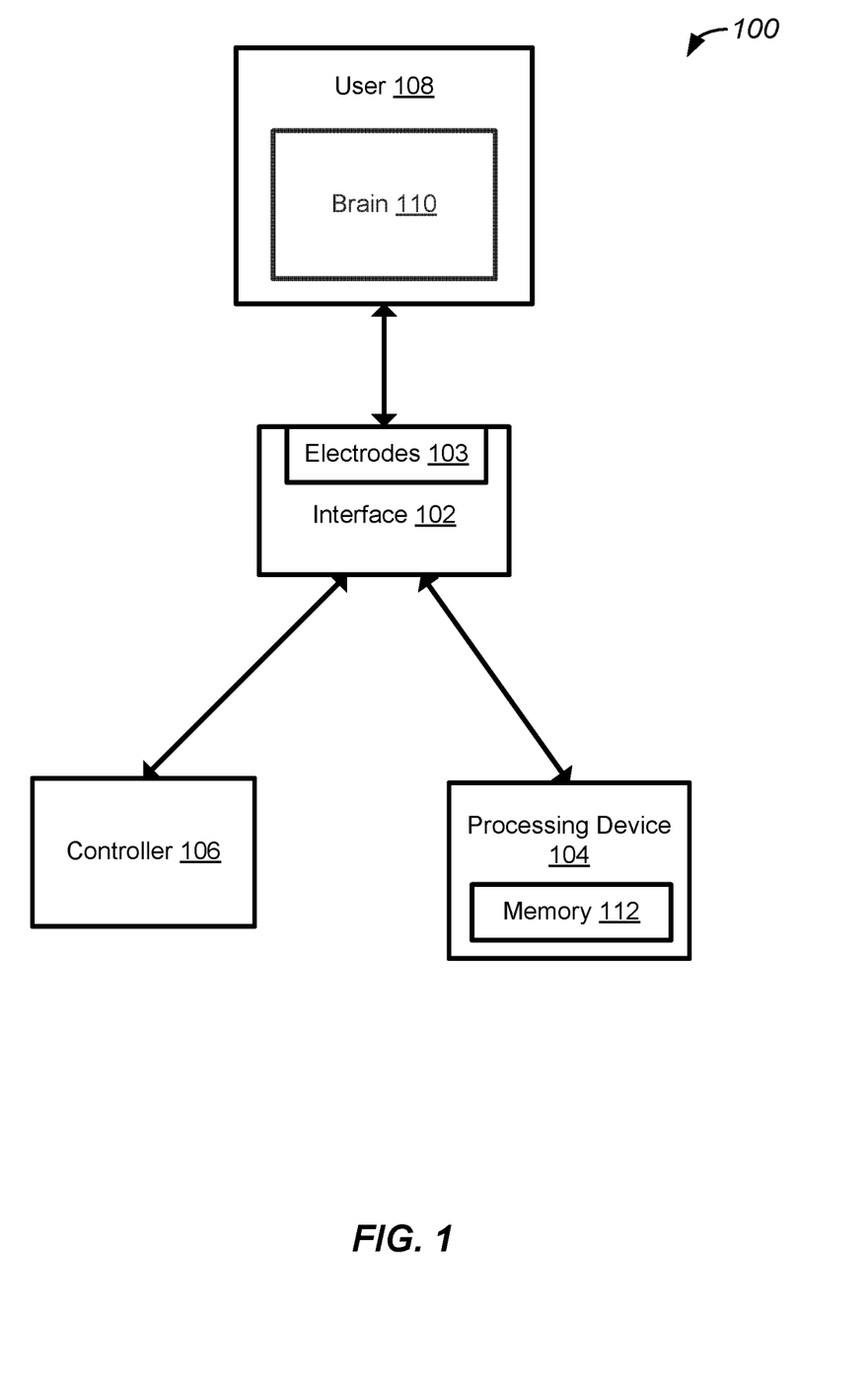
FIG. 1 illustrates an example of a system for providing biomarker shaping and sleep enhancement, configured in accordance with some embodiments.

FIG. 1 illustrates an example of a system for providing biomarker shaping and sleep enhancement, configured in accordance with some embodiments. As will be discussed in greater detail below, a user may have a sleep profile that describes aspects of the user's sleep, and such sleep profiles may be defined, in part, by biomarkers. Embodiments disclosed herein enable the identification and modification of such biomarkers to custom tailor the user's sleep profile to an ideal target sleep profile.

As will be discussed in greater detail below, components of system 100 may be implemented to provide enhancement of sleep profiles of a user, such as user 108. As shown in FIG. 1, user 108 may be a person, and may be coupled to components of system 100. More specifically, brain 110 of user 108 may be coupled to system 100 such that system 100 is able to monitor and measure neural activity within brain 110. In some embodiments, the activity is electrical activity that is measured and recorded as electrical measurements. In this way, activity within brain 110 may be monitored during a period of sleep. As will also be discussed in greater detail below, the coupling between user 108 and system 100 may also enable stimulation of neurons within brain 110. Accordingly, system 100 may also modify neural activity of user 108.

In various embodiments, coupling between user 108 and system 100 may be implemented, at least in part, via an interface, such as interface 102. In one example, interface 102 includes a plurality of electrodes, such as electrodes 103. More specifically, such electrodes may be implemented as an electrode array. Such electrodes may be included in a scalp potential electroencephalogram (EEG) array, may be deep brain stimulation (DBS) electrodes such as electrodes used with intracranial electroencephalography, or may be an epidural grid of electrodes. In other examples, the electrodes may include optogenetics mechanisms for monitoring various neuronal processes or blood saturation levels. Mechanisms may be used to make various measurements and acquire measurement signals corresponding to neural activity, heart activity, temperature, and/or body/head/eye movements. As used herein, neural activity may refer to spiking or non-spiking activity/potentiation; heart activity may refer to beat rate or beat-to-beat variability; and eye activity may include movements such as micro and macro saccades, as well as slow and rapid eye movements.

In various embodiments, such measured signals may be electrical signals derived based on neural activity that may occur in cortical tissue of a brain, or may include electrical and optical signals derived from the peripheral parts of the user. Such measurements may be acquired and represented in a time domain and/or frequency domain. In this way, activity may be monitored and measured over one or more temporal windows, and such measurements may be stored and utilized by system 100. In various embodiments, such neural activity may be observed for particular regions of cortical tissue determined, at least in part, based on a configuration of interface 102. In one example, this may be determined based on a configuration and location of electrodes included in interface 102 and coupled with the brain.

According to some embodiments, one or more components of interface 102 are configured to provide stimuli to the brain coupled with interface 102. For example, one or more electrodes included in interface 102 may be configured to provide electrical stimuli to cortical tissue of the brain. As discussed above, such electrodes may be implemented utilizing one or more of various modalities which may be placed on a user's scalp, or implanted in the user's brain. As will be discussed in greater detail below, applied stimuli may include applied electrical stimulation at a sleep frequency (for example, a slow wave regime having frequencies of 0-0.5 or 0-1 Hz, in a delta band 1-4 Hz, in a theta band 4-8 Hz or in an alpha band 8-12 Hz). The applied stimuli may also include applied electrical stimulation at higher frequencies (for depth stimulation and for reducing stimulation sensation and side effects), while also stimulating at the sleep frequency as a beat frequency of the higher frequencies (for example: 995 Hz and 1000 Hz at lateral locations to create a 5 Hz stimulation beat frequency). In some embodiments, applied stimuli may have a fixed (dc) offset over which the alternating current rides. They may be applied using pairs of electrodes or multiple electrodes stimulating with a single return electrode (HD stimulation).

As will also be discussed in greater detail below, such actuation and stimuli provided by interface 102 may be of many different modalities. For example, stimuli may be aural, visual, and/or tactile as well as being electrical and/or magnetic, or any suitable combination of these. Accordingly, interface 102 may further includes additional components, such as speakers, lights, display screens, and mechanical actuators that are configured to provide one or more of aural, visual, and/or tactile stimuli to a user. In this way, any suitable combination of different modalities may be used. For example, a combination of electrical and aural stimuli may be provided via interface 102. Further still, interface 102 may include different portions corresponding to signal acquisition and stimuli administration. For example, a first portion of interface 102 may include electrodes configured to measure neural activity, while a second portion of interface 102 includes speakers configured to generate aural stimuli. In another example, a third portion of interface 102 may include electrodes to measure an electrocardiogram (ECG) or heart rate of the user, while a fourth portion of interface 102 may include sensors to measure oxygen saturation levels.

In some embodiments, interface 102 further includes one or more dedicated processors and an associated memory configured to obtain and store the measurements acquired at interface 102. In this way, such measurements may be stored and made available to other system components which may be communicatively coupled with interface 102.

System 100 further includes processing device 104 which may be configured to receive measurements made by interface 102, and may be further configured to identify biomarkers and generate sleep profiles for user 108. As will be discussed in greater detail below, biomarkers may be particular patterns or characteristics of neural activity of user 108. For example, a biomarker may be defined by neural activity in a particular frequency band, a shift in such neural activity or frequency spectra of such activity, or a ratio between amounts of activities in different frequency bands. In another example, the biomarker may be defined by the 5 min average of heart rate, 5 min average beat-to-beat heart rate variability, and the root mean square of the successive differences (rmssd). In another example, the biomarker may be defined as the 5 min mean oxygen saturation level or the frequency spectrum of variations in the oxygen saturation level. While examples have been given with 5 minute periods, and suitable period of time may be sued.

In various embodiments, such biomarkers are identified based on the measurements received via interface 102. Accordingly, processing device 104 may be configured to map such biomarkers to particular components or parameters of a sleep profile for user 108. As will be discussed in greater detail below, a sleep profile may include various profile parameters that are used to identify different stages of sleep of user 108 as well as neural activity represented as biomarkers associated with each sleep stage, and transitions and boundaries between such sleep stages. In various embodiments, sleep stages are different stages of sleep that are experienced by the user during a sleep cycle. For example, there may be a first stage N1, a second stage N2, a third stage N3, and random eye movement (REM) sleep. In some embodiments, the first stage N1 is identified by a first drowsy light sleep stage that may be dominated by alpha 8-12 Hz activity. Furthermore, the next stages N1 and N2 may be known to be dominated by theta 4-8 Hz activity, while N2 will have additional spindle band 12-16 Hz and a third stage N3 may be dominated by delta and slow wave activity.

Accordingly, a first biomarker may correspond to a first sleep stage transition, a second biomarker may correspond to a second sleep stage transition, etc. for as many sleep stage transitions are defined by the sleep profile. Moreover, more than one biomarker may be used to identify a sleep stage transition. For example, a first and second biomarker may be associated with a first sleep stage transition. In this way, processing device 104 is configured to generate, based on measurements, a sleep profile that identifies different sleep stages and biomarkers associated with such sleep stages. In various embodiments, sleep stages and biomarkers associated with sleep stages may be generated by a system component, such as a processing device, and may be generated based on observed data obtained during an observation period. For example, a training or observation period may be implemented while the user is sleeping, and measurements may be made by electrodes, and a controller may record the measurements. Accordingly, measurements are made while the user is progressing through different stages of sleep. Moreover, the observation period may also include a portion of time prior to and after sleep. In this way, the measurements may also include measurement data for a wake state prior to and after a sleep cycle. As will be discussed in greater detail below, the measurements may be used to identify and generate biomarkers, and to store biomarkers associated with each sleep stage of a user's sleep cycle.

In some embodiments, the stages of sleep in a sleep cycle may be identified based on the range of slow wave and delta wave activity enhancement, and/or the reduction of beta wave activity. For example, a ratio of slow wave activity and beta wave activity could be used as a metric that identifies the sleep stages (beneficial vs non-beneficial) based on the range of values given by this ratio during sleep (band ratio). In another example, the stages of sleep in a sleep cycle could be identified based on the range of heart rate variability (rmssd), and different rmssd values may be mapped to different sleep stages based on a predetermined mapping.

Furthermore, processing device 104 is configured to generate a target sleep profile for user 108 and associated stimulus parameters. As will be discussed in greater detail below, the target sleep profile represents an ideal sleep profile for user 108. Such an ideal sleep profile can be determined based on previously stored data or aggregated data from the measurement of the user's multiple sleep sessions. Such an ideal sleep profile may be determined based on previously stored data or aggregated data retrieved from other users. In some embodiments, the ideal sleep profile may have been previously determined by an entity, such as a system administrator. For example, an administrator may have determined that a transition from a first sleep stage to a second sleep stage should occur after a designated period of time. In another example, it may be determined to be a specified percent of the total sleep time for the user based on previous measurements. In yet another example, it may be determined to be a specific profile of changes in band ratios through the sleep cycle. In various embodiments, processing device 104 is configured to generate stimulus parameters based on a comparison of the sleep profile of user 108 and the target sleep profile. Accordingly, processing device 104 may generate one or more stimulus parameters that are configured to implement stimulation, via interface 102, that change or modify the sleep profile of user 108 to match the target sleep profile.

In some embodiments, processing device 104 includes memory device 112 which is configured to store measurement data utilized by processing device 104, and is further configured to store biomarker data and sleep profile data generated by processing device 104.

In some embodiments, system 100 includes controller 106 which is configured to generate one or more control signals for electrodes 103, and is also configured to receive measurements from electrodes 103. Accordingly, controller 106 may be configured to implement and control shaping of biomarkers and enhancement of sleep profiles. In various embodiments, controller 106 is communicatively coupled with interface 102, and processing device 104. Accordingly, controller 106 is configured to received inputs from various other system components, and generate signals provided to interface 102 based, at least in part on such inputs. As will be discussed in greater detail below, such outputs may be used to provide actuations to the brain coupled with interface 102. For example, outputs generated by controller 106 may be used to stimulate the brain via one or more components of interface 102. In this way, controller 106 may provide stimuli to the brain via interface 102, may receive biomarker and sleep profile information via other components such as processing device 104, and may generate stimuli based on such received information.

In some embodiments, controller 106 is configured to implement combined control of pharmacological and stimulation inputs. Accordingly, controller 106 may be configured to modify stimulation inputs based on an expected effect of one or more pharmacological agents that may be administered in conjunction with the stimulation. In this way, controller 106 may modify and control administration of stimuli via interface 102 based on an identified pharmacological regimen. In various embodiments, controller 106 is optionally included in system 100. For example, system 100 might not include controller 106, and such generation of control signals and receiving of measurements may be implemented by processing device 104.

Figure 2:
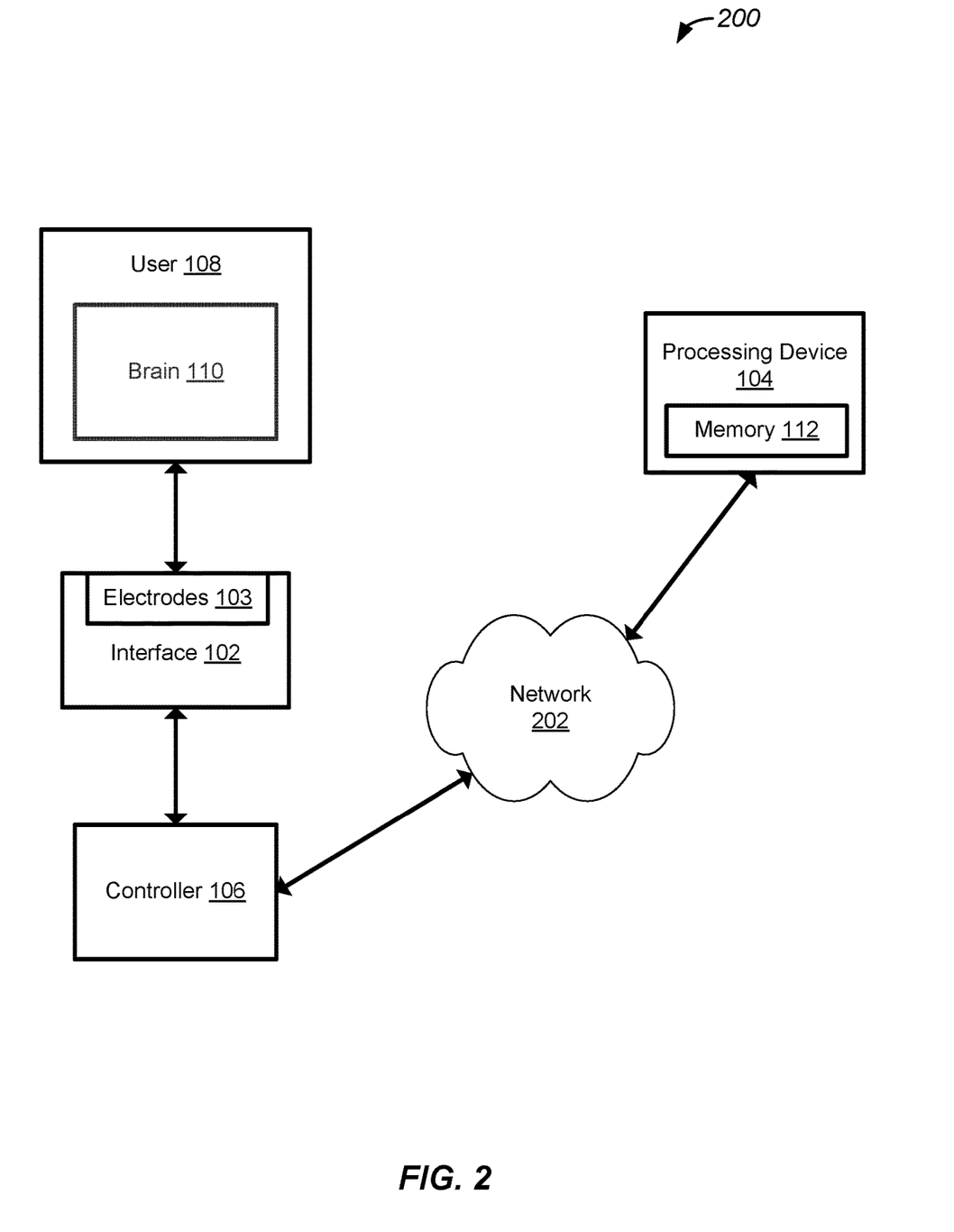
FIG. 2 illustrates another example of a system for providing biomarker shaping and sleep enhancement, configured in accordance with some embodiments.

FIG. 2 illustrates another example of a system for providing biomarker shaping and sleep enhancement, configured in accordance with some embodiments. As similarly discussed above, a user may have a sleep profile that describes aspects of the user's sleep, and such sleep profiles may be defined, in part, by biomarkers. Moreover, systems, such as system 200, may include components such as interface 102, processing device 104, and controller 106, which may be coupled to a user, such as user 108.

As shown in FIG. 2, components of system 200 may be implemented in a distributed manner. For example, controller 106 may be collocated with user 108 and may be communicatively coupled to processing device 104 via a communications network, such as network 202. In this way, controller 106 may be implemented as a wireless device, such as a wearable device, at user 108, processing device 104 may be implemented remotely in a data processing system, and communications between controller 106 and processing device 104 may be handled via a network 202, which may be the internet. In this way, processing device 104 may be implemented as a personal computer or mobile device located near user 108, or processing device may be implemented as part of a distributed computing platform configured to provide sleep profile enhancement as a Software as a Service (Saas) platform.

Figure 3:
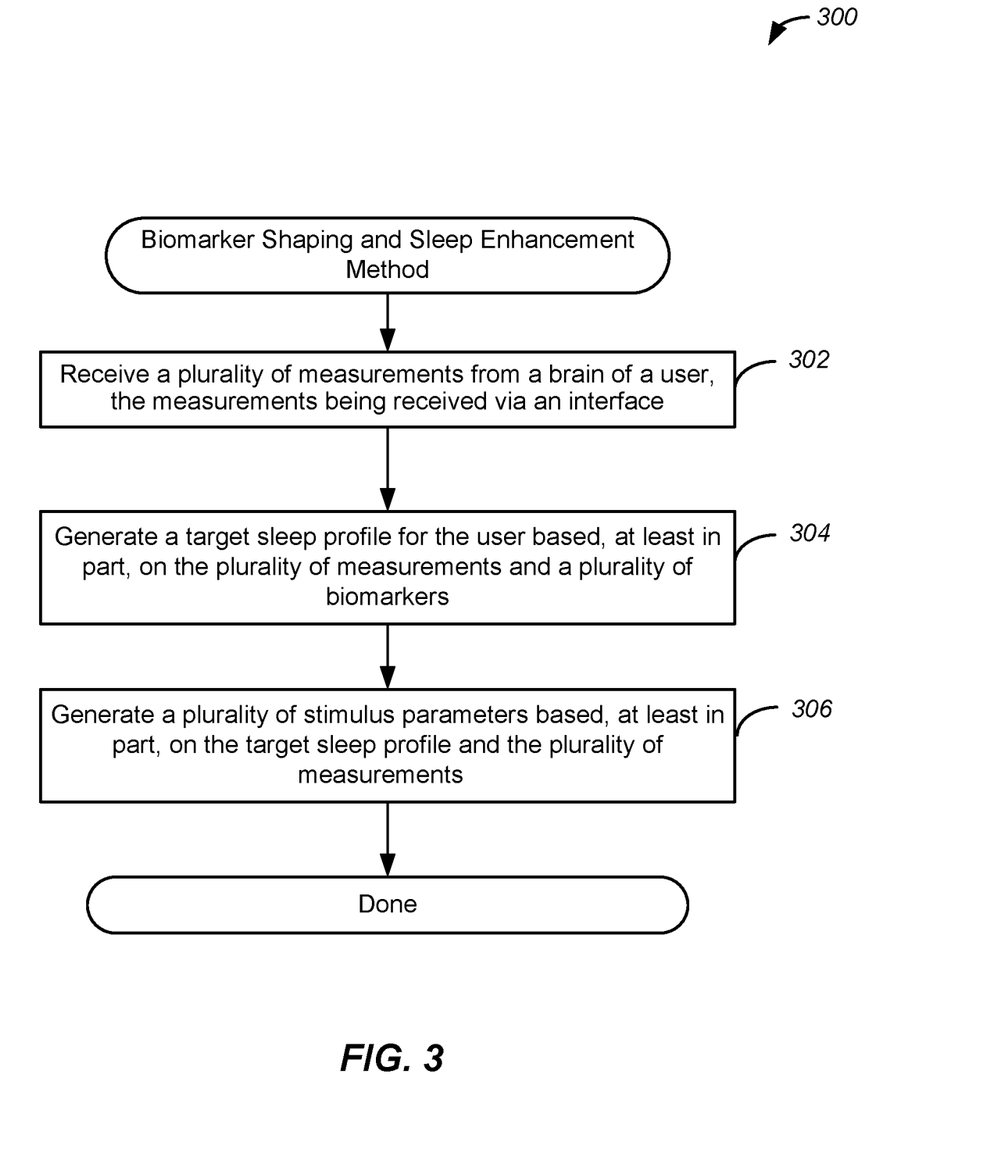
FIG. 3 illustrates an example of a flow chart of a method for providing biomarker shaping and sleep enhancement, implemented in accordance with some embodiments.

FIG. 3 illustrates an example of a flow chart of a method for providing biomarker shaping and sleep enhancement, implemented in accordance with some embodiments. As similarly discussed above, a user may have a sleep profile that describes aspects of the user's sleep, and such sleep profiles may be defined, in part, by biomarkers. Methods disclosed herein, such as method 300, provide the ability to identify and represent a user's current sleep profile, and also generate stimulus parameters to adjust the user's sleep profile to achieve an ideal or target sleep profile.

Method 300 may commence with operation 302 during which a plurality of measurements may be received, via an interface, from a brain of a user. As discussed above, the measurements may be measurements of neural activity made via electrodes included in an interface coupled to the user. The measurements may be provided from the interface to a controller and processing device. Moreover, the measurements may be made while the user is going to sleep, while the user sleeps, and while the user wakes. In this way, measurements are made at all sleep stages of the user. Moreover, the measurements may be used by the processing device to generate a current sleep profile for the user.

Method 300 may proceed to operation 304 during which a target sleep profile may be generated for the user based, at least in part, on the plurality of measurements and a plurality of biomarkers. As discussed above, the target sleep profile may be an ideal sleep profile for the user that represents ideal transition times between sleep stages as well as ideal temporal durations of each sleep stage. In some embodiments, the ideal sleep profile may identify a specific range of values throughout the user's sleep cycle, for example, for the band ratio identified above. It may also identify specific shape or range of values for the heart rate through the user's sleep cycle. The ideal sleep profile may be generated based on previously stored data as well as biographical data associated with the user. For example, the user's age and gender may be used to query a database and identify parameters of a target sleep profile for the user.

Method 300 may proceed to operation 306 during which a plurality of stimulus parameters may be generated based, at least in part, on the target profile. Accordingly, a system component, such as a processing device, may compare the current sleep profile with the target sleep profile and may identify one or more differences between the two profiles. Moreover, the processing device may identify various stimulation parameters based on the identified differences. For example, by stimulating in an alpha frequency range (electrically or auditorily) a user may be induced into the light sleep stage faster. It may also be used to induce the user into deeper stages of sleep faster. It may also be used to enhance or inhibit the spindle activity during sleep stage N2. In another example, stimulating in the theta frequency band and/or low frequency (0.5-1.5 Hz) could enhance the slow wave activity during light and deep sleep stages. In another example, a combination of frequencies of stimulation simultaneously could combine the benefits of the individual band stimulations as discussed above. In yet another example, the sequencing of the different stimulation frequency (all before sleep or during sleep based on the sleep stage they are in) could modify the sleep profile as desired. In this way, the processing device may generate a stimulus regimen that is configured to modify or shape the current sleep profile to match the target sleep profile via stimulation provided by the controller and the interface.

Figure 4:
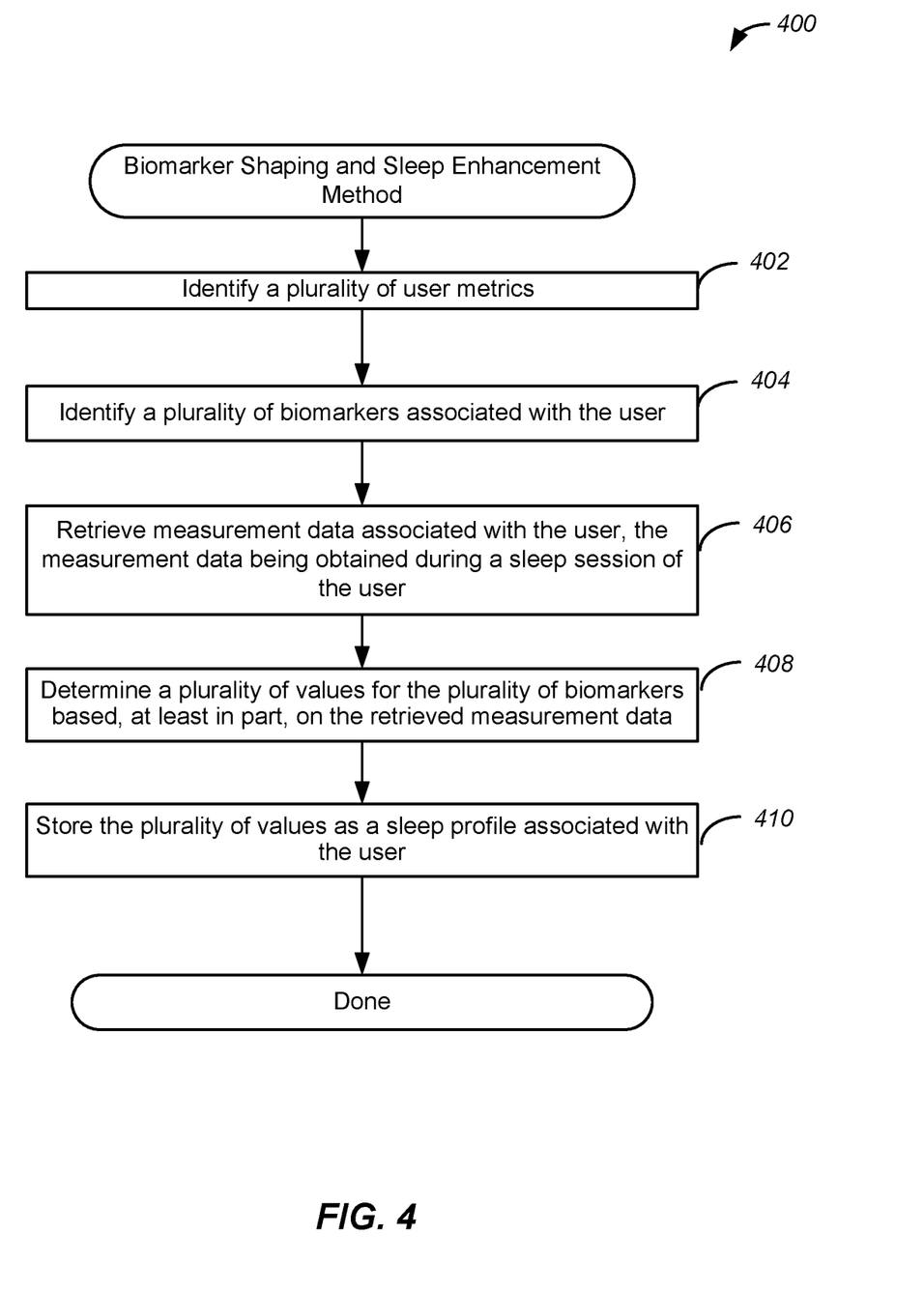
FIG. 4 illustrates another example of a flow chart of a method for providing biomarker shaping and sleep enhancement, implemented in accordance with some embodiments.

FIG. 4 illustrates another example of a flow chart of a method for providing biomarker shaping and sleep enhancement, implemented in accordance with some embodiments. As discussed above, aspects of a user's sleep cycle may be represented as a sleep profile. More specifically, measurement data obtained during the user's sleep cycle may be used to model and represent neural and other activity of the user during the sleep cycle. As will be discussed in greater detail below, a method, such as method 400, may be used to identify particular patterns and characteristics of the user's neural activity that correspond to different sleep stages and transitions between sleep stages.

Method 400 may commence with operation 402 during which a plurality of user metrics may be identified. In various embodiments, the plurality of user metrics may be biological metrics such as age, weight, height, and gender. The user metrics may also include health metrics such as an identification or indication of a health condition or ailment, such as heart disease, sleep apnea, or insomnia. As will be discussed in greater detail below, such user metrics may be used to identify, modify, and/or weight particular biomarkers and their representation in the user's sleep profile.

Method 400 may proceed to operation 404 during which a plurality of biomarkers may be identified. As similarly discussed above, biomarkers may be used to identify particular stages of sleep, as well as transition boundaries between stages of sleep and pre-transition neural activity. More specifically, a user may have many stages of sleep. For example, a user may have a first stage of sleep, a second stage of sleep, a third stage of sleep, a fourth stage of sleep, and rapid eye movement (REM) sleep. Moreover, each stage of sleep may be characterized by a particular pattern of neural activity, and/or combinations of patterns of neural activity. In various embodiments, such patterns of neural activity may be particular frequency bands of activity, ratios of activity in different frequency bands, and shifts in frequency spectra.

Method 400 may proceed to operation 406 during which a measurement data may be retrieved. As discussed above, measurement data may have been obtained via electrodes included in an interface. Accordingly, during operation 406, such measurement data may be retrieved for use by the processing device. In some embodiments, this may occur dynamically and while the measurements are being made. In various embodiments, this may occur after the measurements have already been made, and the measurement data may be retrieved from a memory device. In various embodiments, the measurement data may include data values representing a signal amplitude as well as time course data. Moreover, the measurement data may be pre-processed to include frequency information, such as a representation of a power spectrum.

Method 400 may proceed to operation 408 during which one or more values may be determined for the plurality of biomarkers based, at least in part, on the measurement data. Accordingly, a system component, such as the processing device, may scan the measurement data, and may identify the presence of such biomarkers and compute a value for each of the identified biomarkers if appropriate. For example, the processing device may identify a shift in frequency spectra occurring at a particular time. The processing device may also compute ratios of activity in different frequency bands. If the ratio matches a designated value, a particular stage of sleep may be identified. In some embodiments, if the ratio matches a particular designated value, it may be identified as beneficial or non-beneficial sleep. In various embodiments, such a mapping of biomarkers to sleep stages and transitions between sleep stages may have been previously stored in memory by an entity, such as an administrator. In some embodiments, such a mapping may be retrieved from a database system.

Method 400 may proceed to operation 410 during which the one or more values may be stored as a sleep profile for the user. Accordingly, the values computed for each biomarker, as well as any associated contextual data, may be stored in a memory device as a data object that is the user's sleep profile. As discussed above, and as will be discussed in greater detail below, the user's sleep profile may be used in conjunction with a target sleep profile to custom tailor a stimulation protocol that is configured to enhance the user's sleep and achieve the target sleep profile. While method 400 describes a single iteration of measurement data acquisition and sleep profile determination, it will be appreciated that multiple sleep sessions may be observed, and a sleep profile may be generated based on measurement data acquired across multiple sleep sessions.

Figure 5:
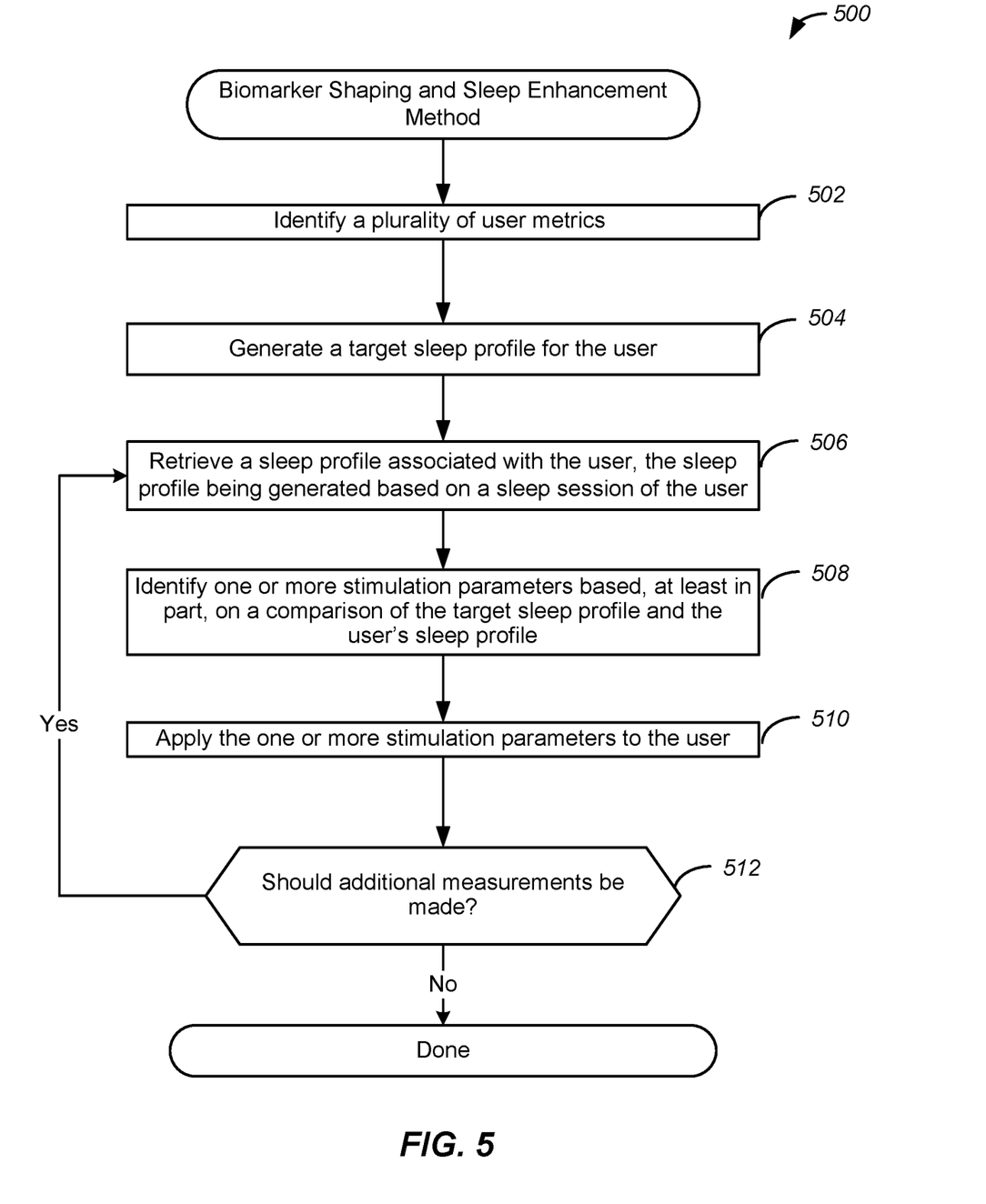
FIG. 5 illustrates an additional example of a flow chart of a method for providing biomarker shaping and sleep enhancement, implemented in accordance with some embodiments.

FIG. 5 illustrates yet another example of a flow chart of a method for providing biomarker shaping and sleep enhancement, implemented in accordance with some embodiments. As discussed above, aspects of a user's sleep cycle may be represented as a sleep profile. Moreover, a target sleep profile may also be generated that represents an ideal sleep profile of the user. As will be discussed in greater detail below, a method, such as method 500, may be used to identify particular stimulus parameters that are configured to modify the user's sleep cycle to better conform to the ideal sleep profile. Moreover, as will also be discussed in greater detail below, the user's sleep profile, the target sleep profile, as well as the stimulation parameters may be dynamically updated such that feedback is provided between, and in some embodiments during, sleep cycles to continually improve the user's sleep profile.

Method 500 may commence with operation 502 during which a plurality of user metrics may be identified. As similarly discussed above, the plurality of user metrics may be biological metrics such as age, weight, height, and gender. The user metrics may also include health metrics such as an identification or indication of a health condition or ailment, such as heart disease, sleep apnea, or insomnia. As will be discussed in greater detail below, such user metrics may be used to identify, modify, and/or weight particular biomarkers and their representation in a target sleep profile.

Method 500 may proceed to operation 504 during which a target sleep profile may be generated. In various embodiments, the target sleep profile may represent an ideal sleep profile for the user. In some embodiments, the target sleep profile may be provided by an entity, such as an administrator, and such a target sleep profile may be stored in memory. In one example, the target sleep profile may be generated based on an aggregation of previously measured data from numerous other users that may have similar metrics as the user. For example, the target sleep profile may be determined based on averaged measurement data from multiple users having a similar age and gender as the user.

Method 500 may proceed to operation 506 during which a user's sleep profile may be retrieved. As discussed above with reference to FIG. 4, the user's sleep profile may have been previously determined and stored in memory based on an observation period in which measurements were made while the user slept. Moreover, as discussed above, the sleep profile may have been determined based on multiple sleep sessions.

Method 500 may proceed to operation 508 during which one or more stimulation parameters may be identified. Thus, according to various embodiments, the user's sleep profile may be compared with the target sleep profile, and stimulation parameters may be identified based on one or more identified differences between the user's sleep profile and the target sleep profile. In one example, the identified differences may be differences in values of biomarkers. Moreover, such differences in biomarkers may be mapped to particular stimulation parameters. The mapped stimulation parameters could include intensity of stimulation, frequency/frequencies of stimulation, duration(s) of stimulation, location of stimulation, and sequencing of the various stimulation waveforms. In various embodiments, such a mapping of differences in biomarkers to stimulation parameters may have been previous stored in memory by an entity, such as an administrator. In various embodiments, stimulation parameters may also be defined by dominant or characteristic aspects of the stages of sleep themselves. For example, application of stimuli at 10 Hz may make the user drowsy and get to stage N1 faster. Furthermore, when in N1, stimulation may be applied at 5 Hz and could help guide the user to N2 faster. Further still, when in N2, stimulation could be applied at 1 Hz and could guide the user to N3 faster. In this way, the stimulation parameters may be determined and applied to affect the onset and durations of sleep stages. In some embodiments, the frequency of stimulation may be customized to specific dominant frequencies measured in the user. For example, for a user it might be more efficacious to stimulate at 9.4 Hz instead of 10 Hz to induce sleep faster.

Method 500 may proceed to operation 510 during which the one or more stimulation parameters may be applied. Accordingly, a system component, such as a controller, may utilize the stimulation parameters to implement a stimulation protocol via the use of an interface and electrodes included in the interface. The stimulation protocol may be administered during the user's sleep session and/or prior to the user falling asleep. In various embodiments, the waking of a user is the last step of their sleep profile. Accordingly, specific stimulation parameters used in stimulating the user postsleep can also be used to shape their target sleep profile. In some examples, the waking stimulation may be configured and determined by implementing the reverse of the stimulation parameters used to induce sleep. In another example, the waking stimulation may be specifically configured to enhance specific higher frequencies of stimulation that are used to enhance alertness in the user when waking and finishing their sleep cycle. In this way, stimulation may be applied to the user in order to modify or shape the user's biomarkers. From example, stimulation may be applied to initiate a shift in frequency spectra earlier than would occur based on the user's own natural rhythm. In another example, stimulation may be applied to achieve a particular ratio of activity in different frequency bands during a particular stage of sleep. In another example, the stimulation may be applied to achieve a specific range of heart rate variability (rmssd) during a particular stage of sleep.

Method 500 may proceed to operation 512 during which it may be determined if additional measurements should be made. In various embodiments, such a determination may be made based on whether or not additional modification of the user's sleep profile is desired. Such a determination may be made based on a comparison of an updated sleep profile. For example, if the updated sleep profile of the user is still different than the target sleep profile, it may be determined that additional modification should be implemented, and method 500 may proceed to operation 506. If it is determined that no additional modification should be made, method 500 may terminate.

Figure 6:
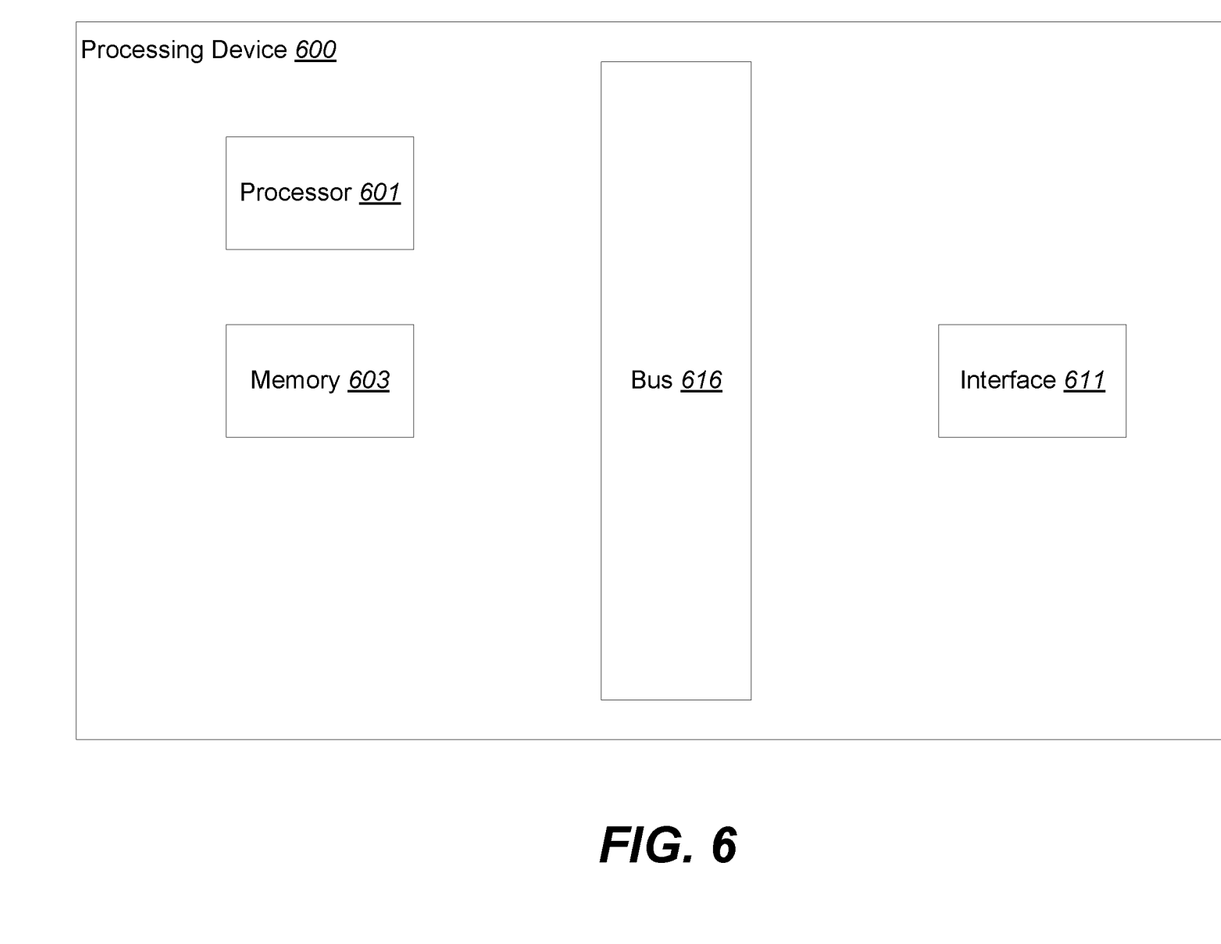
FIG. 6 illustrates an example of a processing device that can be used with various embodiments.

FIG. 6 illustrates an example of a processing device that can be used with various embodiments. For instance, the processing device 600 can be used to implement any of processing device 104 and controller 106 according to various embodiments described above. In addition, the processing device 600 shown can be implemented in conjunction with a computing system on a mobile device or on a computer or laptop, etc. According to particular example embodiments, a processing device 600 suitable for implementing particular embodiments of the present invention includes a processor 601, a memory 603, an interface 611, and a bus 616 (e.g., a PCI bus). The interface 611 may include separate input and output interfaces, or may be a unified interface supporting both operations. When acting under the control of appropriate software or firmware, the processor 601 is responsible for tasks such as closed loop control. Various specially configured devices can also be used in place of a processor 601 or in addition to processor 601. The complete implementation can also be done in custom hardware. The interface 611 may be configured to send and receive data packets or data segments over a network. Particular examples of interfaces the device supports include Ethernet interfaces, frame relay interfaces, cable interfaces, DSL interfaces, token ring interfaces, and the like. In various embodiments, interface 611 may also be a wired connection or a bus with appropriate communications ports.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the processing device 600 uses memory 603 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present invention relates to tangible, machine readable media that include program instructions, state information, etc. for performing various operations described herein. Examples of machine-readable media include memory devices such as non-volatile memory devices, volatile memory devices, and may also utilize optical media such as CD-ROM disks and DVDs, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

While the present disclosure has been particularly shown and described with reference to specific embodiments thereof, it will be understood by those skilled in the art that changes in the form and details of the disclosed embodiments may be made without departing from the spirit or scope of the disclosure. Specifically, there are many alternative ways of implementing the processes, systems, and apparatuses described. It is therefore intended that the invention be interpreted to include all variations and equivalents that fall within the true spirit and scope of the present invention. Moreover, although particular features have been described as part of each example, any combination of these features or additions of other features are intended to be included within the scope of this disclosure. Accordingly, the embodiments described herein are to be considered as illustrative and not restrictive.

What is claimed is:

1. A system comprising:
a plurality of electrodes configured to be coupled to a brain of a user and configured to obtain a plurality of measurements from the brain of the user;
an interface configured to obtain the plurality of measurements from at least the plurality of electrodes; and
a processing device comprising one or more processors configured to:
generate a first target sleep profile for the user based, at least in part, on:
the plurality of measurements and a plurality of biomarkers; and
processing deice being further configured to generate a plurality of electrical brain stimulus parameters to effect a change in a band ratio based on a range of values associated with a ratio of slow wave activity to beta wave activity based, at least in part, on a comparison of the first target sleep profile and a sleep profile of the user,
wherein the first target sleep profile is identified based, at least in part, on a plurality of sleep stages and the plurality of biomarkers, wherein one or more biomarkers of the plurality of biomarkers identify each of the plurality of sleep stages;
wherein the first target sleep profile includes at least one target biomarker that corresponds with a sleep stage transition.

2. The system of claim 1, wherein the plurality of biomarkers comprises a ratio of band activities and shifts in frequency spectra of activity.

3. The system of claim 1, wherein the plurality of stimulus parameters comprises frequencies and amplitudes of stimulation.

4. The system of claim 1 further comprising:
a controller configured to:
generate a control signal based on the plurality of stimulus parameters; and
use the control signal to stimulate the brain of the user via the plurality of electrodes and based on the plurality of stimulus parameters.

5. The system of claim 4, wherein the processing device is further configured to generate a second target sleep profile after the stimulation of the brain of the user.

6. The system of claim 4, wherein the processing device generates a stimulus regimen that is configured to modify or shape the sleep profile of the user to match the first target sleep profile via stimulation provided by the controller and the interface.

7. The system of claim 1, wherein the plurality of sleep stages is identified based on a metric corresponding to a ratio of slow wave activity to beta wave activity.

8. The system of claim 1, wherein the plurality of sleep stages is identified based on a range of heart rate variability, wherein different ranges of heart rate variability values are mapped to different stages based on a predetermined mapping.

9. The system of claim 1, wherein the plurality of sleep stages is identified by a reduction in beta wave activity.

10. The system of claim 1, wherein the first target sleep profile is generated based on biographical data associated with the user.

11. The system of claim 1, wherein to generate the first target sleep profile, the processing device is configured to:
identify a plurality of user metrics, including a plurality of biological metrics and a plurality of health metrics;
receive an aggregation of previously measured data from numerous other users that have similar metrics as the plurality of user metrics; and
determine the first target sleep profile based on the aggregation of the previously measured data.

12. The system of claim 1, wherein to generate the plurality of stimulus parameters, the processing device is configured to:
identify, based on the comparison between the first target sleep profile and the sleep profile of the user, one or more differences between the first target sleep profile and the sleep profile of the user; and
identify the plurality of stimulus parameters based on the identified one or more differences between the first target sleep profile and the sleep profile of the user.

13. The system of claim 12, wherein the one or more differences includes differences in values of the plurality of biomarkers, wherein the differences in the values of the plurality of biomarkers are mapped to the plurality of stimulus parameters, the mapped stimulus parameters including intensity of stimulation, frequency of stimulation, duration of stimulation, location of stimulation, and sequencing of stimulation waveforms.

14. The system of claim 1, wherein the plurality of stimulus parameters comprises:
stimulus parameters related to a stimulus in an alpha frequency range; and
stimulus parameters related to a stimulus in a theta frequency band or a delta frequency band.

15. A device comprising:
an interface configured to obtain a plurality of measurements from a plurality of electrodes configured to be coupled to a brain of a user;
a processing device comprising one or more processors configured to:
generate a first target sleep profile for the user based, at least in part, on:
the plurality of measurements and a plurality of biomarkers; and
a target band ratio based on a range of values associated with a ratio of target slow wave activity to target beta wave activity; and
generate a plurality of electrical brain stimulus parameters based, at least in part, on a comparison of the first target sleep profile and a sleep profile of the user, wherein the plurality of electrical brain stimulus parameters effects an adjustment of a band ratio of the sleep profile to the target band ratio; and
a controller comprising one or more processors configured to generate a control signal based on the plurality of stimulus parameters,
wherein the first target sleep profile is identified based, at least in part, on a plurality of sleep stages and the plurality of biomarkers, wherein one or more biomarkers of the plurality of biomarkers identify each of the plurality of sleep stages;
wherein the first target sleep profile includes at least one target biomarker that corresponds with a sleep stage transition.

16. The device of claim 15, wherein the processing device is further configured to generate the first target sleep profile for the user based, at least in part, on a percent of time that a transition from a first sleep stage to a second sleep stage occurs with respect to a percent of total sleep time.

17. The device of claim 15, wherein the controller is further configured to use the control signal to stimulate the brain of the user via the plurality of electrodes and based on the plurality of stimulus parameters.

18. A method comprising:
receiving, via an interface and a plurality of electrodes coupled to a brain of a user, a plurality of measurements from the brain of the user;
generating, using one or more processors of a processing device, a first target sleep profile for the user based, at least in part, on the plurality of measurements and a plurality of biomarkers; and
generating, using the one or more processors of the processing device, a plurality of electrical brain stimulus parameters that adjusts a band ratio associated with the plurality of measurements to a target band ratio associated with the first target sleep profile based, at least in part, on a comparison of the first target sleep profile and a sleep profile of the user, wherein the band ratio and the target band ratio are each based on a range of values associated with a ratio of slow wave activity and beta wave activity, respectively,
wherein the first target sleep profile is identified based, at least in part on a plurality of sleep stages and biomarkers identifying each of the plurality of sleep stages;
wherein the first target sleep profile includes at least one target biomarker that corresponds with a sleep stage transition.

19. The method of claim 18, wherein the plurality of stimulus parameters comprises frequencies and amplitudes of stimulation.

20. The method of claim 18 further comprising:
generating, using a controller, a control signal based on the plurality of stimulus parameters, and
using the control signal to stimulate the brain of the user via the plurality of electrodes and based on the plurality of stimulus parameters.

* * * * *